United States Patent
Stier et al.

(10) Patent No.: US 9,804,057 B2
(45) Date of Patent: Oct. 31, 2017

(54) SEALED CABLE PASSAGE FOR AN EXHAUST-GAS SENSOR

(71) Applicant: Robert Bosch GmbH, Stuttgart (DE)

(72) Inventors: Joachim Stier, Bad Liebenzell (DE); Guido Soyez, Ludwigsburg (DE); Jens Schneider, Leonberg (DE); Bernd Rattay, Ditzingen (DE); Andreas Opp, Rutesheim (DE); Axel Klenner, Weil Der Stadt (DE); Rainer Maier, Tamm (DE); Peter Winkler, Leonberg (DE)

(73) Assignee: ROBERT BOSCH GMBH, Stuttgart (DE)

( * ) Notice: Subject to any disclaimer, the term of this patent is extended or adjusted under 35 U.S.C. 154(b) by 112 days.

(21) Appl. No.: 14/399,725

(22) PCT Filed: Mar. 15, 2013

(86) PCT No.: PCT/EP2013/055437
§ 371 (c)(1),
(2) Date: Nov. 7, 2014

(87) PCT Pub. No.: WO2013/167301
PCT Pub. Date: Nov. 14, 2013

(65) Prior Publication Data
US 2015/0128681 A1    May 14, 2015

(30) Foreign Application Priority Data
May 9, 2012   (DE) .................... 10 2012 207 762

(51) Int. Cl.
B29C 70/84   (2006.01)
H02G 15/23   (2006.01)
(Continued)

(52) U.S. Cl.
CPC .......... *G01M 15/102* (2013.01); *B29C 70/84* (2013.01); *G01N 27/4078* (2013.01);
(Continued)

(58) Field of Classification Search
CPC ........................ G01N 27/409; G01N 27/407
(Continued)

(56) References Cited

U.S. PATENT DOCUMENTS 5,602,325 A * 2/1997 McClanahan ...... G01N 27/4062
                                                       204/424
5,874,664 A * 2/1999 Watanabe ............ G01N 27/407
                                                       73/23.32
(Continued)

FOREIGN PATENT DOCUMENTS

CN    1232579 A    10/1999
CN    1618155 A    5/2005
(Continued)

OTHER PUBLICATIONS

International Search Report for PCT/EP2013/055437, dated Mar. 15, 2013.

*Primary Examiner* — Michael F McAllister
(74) *Attorney, Agent, or Firm* — Norton Rose Fulbright US LLP; Gerard Messina (57) ABSTRACT

A cable passage for sealing and for electrically contacting an exhaust-gas sensor includes: a protective sleeve; and at least one connecting cable which is run out of the protective sleeve on at least one front side of the protective sleeve. At least one cross section of the space existing between the protective sleeve and the at least one connecting cable is filled with a thermoplastically workable fluoropolymer-containing material.

17 Claims, 9 Drawing Sheets

(51) Int. Cl.
*G01M 15/10* (2006.01)
*G01N 27/407* (2006.01)
*H02G 15/00* (2006.01)
*B29K 27/12* (2006.01)
*B29K 105/00* (2006.01)
*B29L 9/00* (2006.01)
*B29L 31/34* (2006.01)

(52) U.S. Cl.
CPC ........... *H02G 15/003* (2013.01); *H02G 15/23* (2013.01); *B29K 2027/12* (2013.01); *B29K 2105/0058* (2013.01); *B29L 2009/00* (2013.01); *B29L 2031/3462* (2013.01)

(58) Field of Classification Search
USPC ........................................ 174/77 R, 264, 262
See application file for complete search history.

(56) References Cited

U.S. PATENT DOCUMENTS

| | | | | |
|---|---|---|---|---|
| 5,949,023 | A * | 9/1999 | Weyl | G01N 27/4062 |
| | | | | 174/652 |
| 6,039,856 | A * | 3/2000 | Weyl | G01N 27/4077 |
| | | | | 204/400 |
| 2004/0244467 | A1 * | 12/2004 | Yamada | G01N 27/407 |
| | | | | 73/31.05 |
| 2007/0033986 | A1 * | 2/2007 | Wild | G01N 37/00 |
| | | | | 73/31.05 |
| 2007/0281166 | A1 * | 12/2007 | Nishio | B32B 7/02 |
| | | | | 428/421 |

FOREIGN PATENT DOCUMENTS

| | | | |
|---|---|---|---|
| DE | 94 10 070 | | 10/1995 |
| DE | 101 51 291 | | 5/2002 |
| DE | 102 34 266 | | 2/2004 |
| DE | 10 2005 020 793 | | 11/2006 |
| DE | 10 2007 017 999 | | 10/2008 |
| EP | 0 702 229 | | 3/1996 |
| JP | H04285849 | | 10/1992 |
| JP | H063319 A | | 1/1994 |
| JP | H0862176 A | | 3/1996 |
| JP | H11 190717 | | 7/1999 |
| JP | 2001 103645 | | 4/2001 |
| JP | 2001-242128 | * | 9/2001 |
| JP | 2005 134299 | | 5/2005 |
| JP | 2011003645 A | | 1/2011 |
| WO | WO 97 36172 | | 10/1997 |

* cited by examiner

SEALED CABLE PASSAGE FOR AN EXHAUST-GAS SENSOR

BACKGROUND OF THE INVENTION

1. Field of the Invention

The present invention relates to an exhaust-gas sensor which includes a housing body, in which a sensor element is located that is made of ceramic for example and that operates electrochemically, and a cable outlet welded to the housing body that seals the housing body and electrically contacts the sensor element, which cable outlet has a for example metallic protective sleeve and one or several connecting cables leading out of the protective sleeve.

2. Description of the Related Art

On the one hand, a high degree of seal tightness is required of the cable outlet and its interaction with the housing body of the exhaust-gas sensor. The high degree of seal tightness effectively and permanently prevents the intrusion of harmful liquids and gases, which could trigger corrosion for example, into the interior of the exhaust-gas sensor. In order to realize the seal tightness, the cable outlet must provide in particular a sufficiently tight, durable and temperature-resistant seal between the protective sleeve and the connecting cables.

Published German patent application document DE 10 2005 020 793 A1 already discloses providing a prefabricated stopper made from polytetrafluoroethylene, also known as PTFE, for sealing a front side of the protective sleeve of an exhaust-gas sensor. There is furthermore a provision for welding insulating jackets of connecting cables in passage channels of this stopper using fluorine-containing plastic and to provide a force-locking seal between the protective sleeve and the stopper using a tube made of fluorine-containing plastic.

In the sensor known from the related art, sealing in the area of the protective sleeve requires handling a multitude of discrete, preformed components made of different materials. This makes the manufacturing process comparatively costly.

BRIEF SUMMARY OF THE INVENTION

Exhaust-gas sensors according to the present invention and cable passages according to the present invention, by contrast, are simple to manufacture and exceedingly reliable.

The present invention provides for a cable passage for an exhaust-gas sensor. In the present context, an exhaust-gas sensor is to be understood in particular as a lambda probe for use in the exhaust tract of a burner or a combustion engine, but may also refer to other sensors such as a temperature sensor or an NOx sensor or soot particle sensor or the like as well as sensors that are provided for continuous use at high temperatures and/or in an aggressive environment, and sensors in which a for example electrical connector cable is to be run out of a housing to be sealed, particularly at comparatively high ambient temperatures, for example at up to 260° C. An exhaust-gas sensor is in particular to be understood as a device provided for installation, for example a screw-in installation, in an exhaust tract of a burner and/or a combustion engine.

The cable passage according to the present invention has a protective sleeve. This is in particular a tube that is open on one side or on two sides, having in particular an axial symmetry. Smaller deviations from an axial symmetry, such as geometrical inaccuracies and/or smaller structural details, are possible as well such that even in this case it is still possible to assume an axial geometry with respect to the basic shape of the protective sleeve. An axis of the sensor is also given by the sleeve shape of the protective sleeve, and the resulting terminology (axial, lateral etc.) is used in connection with the present application.

The protective sleeve may be for example a deep-drawn part, for example a part that has a wall thickness of one millimeter or less. It is preferably a metallic protective sleeve, made from stainless steel for example. Different specific embodiments of the protective sleeve are possible in principle, for example the provision of sections, disposed axially in succession, of varying, in particular narrowing, diameters and/or steps situated between these sections and the like.

The cable passage according to the present invention furthermore has at least one, that is, one or more, connecting cable(s). In particular, there may be two, three, four, five or six connecting cables. Another number of connecting cables, such as seven connecting cables for example, is also possible in principle and is not shown explicitly in the present case only for reasons of keeping the presentation concise.

Although the term connecting cable is presently not to be understood in an excessively restrictive manner, it is nevertheless preferred that the connecting cable includes a metallic electric conductor, for example a stranded wire made of copper or a stranded wire made of steel and copper. Furthermore, the present invention provides in particular for the connecting cable or the metallic electric conductor to be surrounded entirely or partially by an insulation, in particular entirely or partially in the area in which the connecting cable is in contact with the thermoplastically workable fluoropolymer-containing material, and/or in the area in which the connecting cable is run out of the protective sleeve on at least one front side of the protective sleeve. The connecting cable in particular has an insulation made of polytetrafluoroethylene (PTFE), which has a very high temperature resistance. Other highly temperature-resistant insulations are also possible. In the case of multiple connecting cables, these may be discrete with respect to one another or, by way of a common insulation for example, may be bundled and/or fixed in place relative to one another. In the case of multiple connecting cables, which have an insulation made of polytetrafluoroethylene (PTFE) for example, it is in particular possible to provide for the connecting cables to be spaced apart from one another by the thermoplastically workable fluoropolymer-containing material that is provided in accordance with the present invention.

The present invention provides for the connecting cable or, in the case of multiple connecting cables, the connecting cables to be run out of the protective sleeve on a front side of the protective sleeve. In particular, there remains a space between the protective sleeve and the connecting cable(s), that is, a space in the interior of the protective sleeve that is not filled by the connecting cable(s). Although this space is in principle not limited in terms of its shape, it is conceivable that it includes the gaps forming between the connecting line or connecting lines and the protective sleeve and, in the case of multiple connecting lines, additionally the gaps possibly forming between the connecting lines. In particular, the space between the protective sleeve and the connecting cable(s) may be formed by the totality of the mentioned gaps. Gaps having a width of at least 0.25 mm are preferred since it is easy to introduce into them a thermoplastically workable fluoropolymer-containing material, in particular if it is molten. Thus, for example, molten thermoplastically workable material is readily able to flow into such gaps and/or may be readily injected into such gaps. This is the case particularly in gaps of a width of at least 0.6 mm. On the other hand, gaps of a width of at most 0.4 mm are preferred since in this case the quantity of the thermoplastically workable fluoropolymer-containing material to be introduced or the cross-sectional area to be sealed is not too large and is thus not mechanically unstable or fragile. In particular, an adhesion of the molten thermoplastically workable material is ensured in such narrow gaps, which prevent the molten thermoplastically workable fluoropolymer-containing material from flowing away from its designated location. This is the case particularly in gaps of a width of at most 1.25 mm.

The connecting cables in particular do not touch one another within the cable passage and/or along the axial extension of the cross sections filled with the thermoplastically workable fluoropolymer-containing material.

It is essential for the present invention that at least one cross section of the space existing between the protective sleeve and the at least one connecting cable is filled with a thermoplastically workable fluoropolymer-containing material. A cross section in this connection is to be understood in particular as a plane parallel to the at least one front side of the protective sleeve, in particular in the area of this front side, that is, in particular in the third of the protective sleeve facing the front side. The front side, or the front-side opening of the protective sleeve itself, may also be considered as the cross section.

On the other hand, this cross section may also lie in particular in a plane that is perpendicular with respect to the longitudinal axis of the protective sleeve or one that is tilted against this axis by no more than 30°, preferably by no more than 10°.

Although the essence of the present invention is already fundamentally expressed in the filling of a merely, as it were, planar cross section of the space existing between the protective sleeve and the at least one connecting cable with a thermoplastically workable fluoropolymer-containing material, a particularly good sealing effect is achieved in further developments of the present invention in that the area of the space existing between the protective sleeve and the at least one connecting cable filled with a thermoplastically workable fluoropolymer-containing material extends for a stretch, for example at least 0.5 or at least 2.5 millimeters, preferably even 5 or 7 millimeters, in the axial direction, that is, in particular along the at least one connecting cable. Within the present invention, the term cross section may always be developed further in this sense.

The cross section of the space existing between the protective sleeve and the at least one connecting cable may be developed in particular as lying in one plane. The present invention, however, also comprises cross sections that do not lie completely within one single plane, but are curved for example. Cross sections in the sense of the present invention are in particular also arbitrary planes that divide the space existing between the protective sleeve and the at least one connecting cable into two at least imaginary disjunctive subspaces, of which one, starting from this plane, faces the front side of the protective tube and the other faces away from the front side of the protective tube.

Filling a cross section of the space existing between the protective sleeve and the at least one connecting cable with a thermoplastically workable fluoropolymer-containing material is to be understood in particular in such a way that the gaps remaining along this cross section between the connecting cable or the connecting cables and the protective sleeve and, in the case of multiple connecting lines, additionally the gaps possibly forming between the connecting lines, are filled at least macroscopically completely with the thermoplastically workable fluoropolymer-containing material.

If the thermoplastically workable fluoropolymer-containing material should have pores at a microscopic scale, then these are naturally neglected for the interpretation of the term "filling".

Although theoretically a multitude of fluoropolymer-containing materials may be used in order to fill a cross section of the space existing between the protective sleeve and the at least one connecting cable, the present invention provides exclusively thermoplastically workable materials for this purpose. Polytetrafluoroethylene (PTFE) does not belong to the thermoplastically workable materials since it decomposes chemically already below its (fictitious) melting temperature, that is, already in the solid state, starting at the point at which the decomposition temperature is reached. Fluoroelastomers in particular are also excluded for similar reasons, in particular fluororubbers (FKM) and/or perfluororubbers (FFKM), tetrafluoro ethylene/propylene rubbers (FEPM) and/or fluorinated silicone rubbers.

Investigations on the part of the applicant, by contrast, have identified perfluoroalkoxy polymer (PFA) and tetrafluoroethylene-perfluoropropylene (FEP) as preferred thermoplastically workable fluoropolymer-containing materials.

The materials polychlorotrifluoroethylene (PCTFE) and polyvinylidene fluoride (PVDF) were also identified as suitable. Due to their somewhat lower temperature resistance in comparison to perfluoroalkoxy polymer (PFA) and tetrafluoroethylene-perfluoropropylene (FEP), however, the materials polychlorotrifluoroethylene (PCTFE) and polyvinylidene fluoride (PVDF) are to be provided in particular only for use in lower working temperatures (for example for working temperatures below 210° C.). The use of perfluoroalkoxy polymer (PFA) and tetrafluoroethylene-perfluoropropylene (FEP) are the preferred solution particularly for high working temperatures (for example for working temperatures up to 280° C. or even up to 305° C.)

Although it is preferred for the thermoplastically workable fluoropolymer-containing material to be made of perfluoroalkoxy polymer (PFA) or tetrafluoroethylene-perfluoropropylene (FEP) or polychlorotrifluoroethylene (PCTFE) or polyvinylidene fluoride (PVDF), it may also be mixtures of these substances or materials that contain these substances only in a certain proportion, preferably at least 50%, particularly preferably at least 75%.

Fluoropolymer-containing materials are particularly preferred that are thermoplastically workable and have a melting point or melting range between 170° C. and 320° C., in particular of at least 260° C.

Tetrafluoroethylene-perfluoropropylene (FEP) is understood in this context in particular as the chemical substance having the structural formula [—CF2-CF2-CF(CF3)-CF2-]n. Tetrafluoroethylene-perfluoropropylene (FEP) is understood in this context in particular as chemical substances that are manufacturable by polymerization of mixtures of the monomer tetrafluoroethylene (TFE) and a proportion of the monomer hexafluoropropylene (HFP) that substantially differs from zero.

Perfluoroalkoxy polymers (PFA) are understood in this context in particular as chemical substances that are manufacturable by polymerization of mixtures of the monomer tetrafluoroethylene (TFE) and a proportion of the monomer perfluoropropyl vinyl ether (PPVE) that substantially differs from zero. Perfluoroalkoxy polymers (PFA) are understood in this context in particular as chemical substances having the structural formula [—CF2-CF2-CF(OR)—CF2-]n, the side group OR being at least one alcoxy group. These are in particular fully fluorinated polymers having at least one alcoxy side chain. Perfluoroalkoxy polymers (PFA) are in particular chemical substances that are thermoplastically workable, are able to wet ceramic, oxidic, glass and/or metal surfaces and are meltable with polytetrafluoroethylene (PTFE). The present invention in particular comprises various PFA grades and/or mixtures of different PFA grades, so-called polyblends. In connection with the present invention, the applicant has particularly positive experiences with the use of PFA polyblends whose melting range lies between 260° C. and 320° C., in particular between 260° C. and 320° C. Preferred polymers have a molar mass of $3*10^5$ to $3*10^6$ g/mol.

Polychlorotrifluoroethylene (PCTFE) in this context is understood in particular as the chemical substance having the structural formula [—CFCl—CF2-]n.

Polyvinylidene fluoride (PVDF) in this context is understood in particular as the chemical substance having the structural formula [—CH2-CF2-]n.

According to the present invention, the cross section of the space existing between the protective sleeve and the at least one connecting cable is filled with a thermoplastically workable fluoropolymer-containing material. The cross section of the space existing between the protective sleeve and the at least one connecting cable is filled in particular with a homogeneous thermoplastically workable fluoropolymer-containing material whose chemical composition is thus essentially unchanged along this cross section. The term homogeneous in this context refers in particular to the macroscopic homogeneity of the material and disregards of course microscopic inhomogeneities. The cross section of the space existing between the protective sleeve and the at least one connecting cable is preferably filled with a single homogeneous thermoplastically workable fluoropolymer-containing material, that is to say, at least one entire cross section existing between the protective sleeve and the at least one connecting cable, for example an entire cross section existing between the protective sleeve and the insulation of the at least one connecting cable, is altogether filled with the single homogeneous thermoplastically workable fluoropolymer-containing material.

In very preferred further developments of the present invention, an integral material connection results in the area of this cross section between the thermoplastically workable fluoropolymer-containing material and the protective sleeve and/or an integral material connection results in the area of this cross section between the thermoplastically workable fluoropolymer-containing material and the connecting cable(s). In particular, an overall integral seal is produced indirectly between the connecting cable(s) and the protective sleeve by the thermoplastically workable fluoropolymer-containing material.

In comparison to the related art, the cable passage is distinguished in particular by the lack of a prefabricated stopper, as is used for example in the sensor disclosed in the related art cited at the outset. A prefabricated stopper is understood in this connection as a stopper that is also called a grommet in the related art, which has one or more axial passages for accommodating respectively one or more electrical connecting cables and is insertable or is inserted into a protective sleeve of an exhaust-gas sensor, in particular in its final shape.

The cable passage according to the present invention and the sensor according to the present invention instead have merely a thermoplastically workable and fluoropolymer-containing material, which is introduced in particular in a liquid state into the interior of the protective sleeve and in that location fills at least one cross section of the space existing between the protective sleeve and the at least one connecting cable, filling it in particular in an integral manner.

There are in principle various ways of introducing the in particular liquid or liquefied thermoplastically workable fluoropolymer-containing material into the interior of the protective sleeve or of the exhaust-gas sensor. Thus it is possible to introduce the material by injection molding or extrusion coating. Alternatively, the protective sleeve may be immersed in a liquid or liquefied thermoplastically workable fluoropolymer-containing material. For this purpose, the front side of the protective sleeve, through which the at least one connecting cable is run out of the protective sleeve, is preferably tilted downward, for example at an angle tilted with respect to the horizontal of 0° to 90°, for example 30° to 60°. When introducing the in particular liquid or liquefied thermoplastically workable fluoropolymer-containing material into the interior of the protective sleeve or of the exhaust-gas sensor, templates may be used as aids, which cover regions of the protective sleeve or of the exhaust-gas sensor that are further away on the exhaust-gas side. Such aids may optionally be removed again after introducing the thermoplastically workable fluoropolymer-containing material or may remain in the protective sleeve or in the exhaust-gas sensor.

Alternatively it is also possible to deposit the thermoplastically workable fluoropolymer-containing material initially in a solid state outside of or within the protective sleeve and then to liquefy it by heating such that it fills at least one cross section of the space existing between the protective sleeve and the at least one connecting cable, subsequent to the flowing processes occurring as a result of the liquefication, and afterwards solidifies again.

The absence of a prefabricated stopper in particular results in the complication that there is in particular no lateral guidance for the connecting cable or connecting cables during the installation of the cable passage, which represents an uncertainty in the manufacturing process and in the finished product. In particular, there is also no strain relief provided for the connecting cables in this case during the installation of the cable outlet. For this reason, special further developments of the present invention provide for the protective sleeve to have at least one holder of the at least one connecting cable. This holder effects in particular a lateral anchorage of the connecting cable(s) and/or a strain relief. The holder is able to provide in particular an axial anchorage.

An additional or alternative function of the holder is to support the thermoplastically workable fluoropolymer-containing material axially, and to do so on the one hand in the finished product, in which the thermoplastically workable fluoropolymer-containing material is in a solid state, and, on the other hand, during the manufacture of the cable passage or during the manufacture of the exhaust-gas sensor. In the case of the latter, the holder prevents the thermoplastically workable fluoropolymer-containing material from penetrating too deeply into the interior of the cable passage or the exhaust-gas sensor.

The shape of the holder may vary, the holder having in particular means for fastening it in the protective sleeve, for example an outer, in particular metallic, annular section that may be welded and/or clamped to the protective sleeve. Additionally or alternatively, the holder in particular has means for anchoring the at least one connecting cable and/or for supporting the thermoplastically workable fluoropolymer-containing material. The function of binding the liquefied thermoplastically workable fluoropolymer-containing material may also be considered additionally or alternatively.

For example, the holder may be an insert that is fastened, in particular welded or clamped, in the interior of the protective sleeve. The holder or insert may have passages for accommodating and anchoring the at least one connecting line. Inserts are also possible that have eyelets and/or hooks and/or intersecting webs that respectively accommodate and anchor in particular the connecting lines. The holder for this purpose is preferably made of metal, for example of stainless steel.

Additionally or optionally, the present invention provides for the protective sleeve to be developed in a cup-shaped manner, that is, in particular as having a bottom and a wall situated circumferentially around its edge. In particular, one or more, for example two, three or four etc., passage openings may be developed in the bottom of the cup, through which respectively one or more, for example two, three or four etc., connecting cables are run. The present invention furthermore provides for at least one cross section of the space existing between the protective sleeve and the at least one connecting cable to be filled in such refinements with a thermoplastically workable fluoropolymer-containing material in such a way that the thermoplastically workable fluoropolymer-containing material is developed at least partially in the area of the at least one passage opening in the bottom of the cup. The advantage of these refinements lies in the fact that the open cross section of the passage opening(s) in the bottom of the cup is in particular reduced in comparison to the cross section of the protective tube away from the cup bottom, amounting to for example no more than 65% or no more than 30%, which makes it possible to achieve a mechanically particularly stable seal of the protective sleeve using a comparatively small amount of thermoplastically workable fluoropolymer-containing material.

Additionally or optionally, there is a provision for the cable passage to have at least one guide piece that is separate from the protective sleeve. A guide piece that is separate from the protective sleeve is to be understood in particular in such a way that the guide piece is neither of one piece with the protective sleeve nor is directly connected to the protective sleeve in an integral manner or in a force-locking manner. An indirect integral connection or force-locking connection may be provided, however, for example in that the solid and/or solidified thermoplastically workable fluoropolymer-containing material is situated on the finished product between the guide piece and the protective sleeve, for example laterally and/or axially between the guide piece and the protective sleeve. The separate guide piece is used in particular for guiding the at least one connecting cable at least laterally such that it is laterally anchored relative to the protective sleeve and, in the case of the existence of at least one second connecting cable, relative to the latter. An axial anchoring of the at least one connecting cable, that is, in particular a strain-relieving effect, may also be provided. The separate guide piece may be developed in the shape of a disk and/or have at least one passage opening, at least one connecting cable being able to be run through or running through each of the at least one passage openings. Additionally or alternatively, the thermoplastically workable fluoropolymer-containing material may be situated at least partially in the area of the at least one passage opening of the guide piece.

The separate guide piece may be developed in particular in a cup-shaped manner, that is, in particular as having a bottom and a wall situated circumferentially around its edge. For this purpose, in particular, at least one passage opening is situated in the bottom of the cup, at least one connecting cable being able to be run through or running through each of the at least one passage openings. In particular, the thermoplastically workable fluoropolymer-containing material is situated at least partially in the interior of the cup. The cup is in particular slipped with its open side over the front side of the protective sleeve, that is, in particular, the wall of the cup-shaped guide piece is slipped over the wall of the protective sleeve. In this process of slipping over, at least a portion of the in particular molten or liquid thermoplastically workable fluoropolymer-containing material enters in particular into the space existing between the protective sleeve and the at least one connecting cable, where it in particular solidifies and subsequently fills at least one cross section of the space existing between the protective sleeve and the at least one connecting cable.

It is expedient that at least portions of the thermoplastically workable fluoropolymer-containing material are situated in the interior of the protective sleeve. Situating all of the thermoplastically workable fluoropolymer-containing material in the interior of the protective sleeve is also fundamentally possible and is a measure that improves the stability of the cable passage. Other specific embodiments provide for the thermoplastically workable fluoropolymer-containing material to protrude axially beyond the at least one front side of the protective sleeve and/or for the thermoplastically workable fluoropolymer-containing material to protrude laterally beyond the lateral surface of the protective sleeve. It is also possible to situate a portion of the thermoplastically workable fluoropolymer-containing material on the outer surface of the protective sleeve. Such allocations of the thermoplastically workable fluoropolymer-containing material are in particular suitable for improving its adhesion to the protective sleeve and in particular for improving the seal and durability of the cable passage.

The integral connection is a connection in which a cohesion of the mating parts is achieved by the forces effective at the molecular level such as is defined, in particular, also in VDI guideline 2232-2004-01. Examples of integral connections are welding, bonding, fusion etc. The integral connection may be in particular a direct integral connection between two mating parts, in which there is a direct interaction between the two mating parts at the molecular level. The integral connection, on the other hand, may also be in particular an indirect integral connection, in which the two mating parts are not directly integrally connected to each other, but are respectively directly integrally connected with at least one third mating part, and, in the case of multiple third mating parts, all of these third mating parts are integrally connected (directly or indirectly) to one another.

Passage openings and holes are to be understood in the context of this application always in particular as holes, preferably having a diameter of 0.5 to 2.5 mm, particularly preferably of 1 to 2 mm or having a cross-sectional area of 0.25 to 6 mm$^2$, particularly preferably of 1 to 4 mm$^2$.

It is preferred that the measures according to the present invention result in a connection-side seal tightness of the housing of the exhaust-gas sensor that is comparatively high, for example a helium seal tightness of less than $10^{-3}$ mbar*l/s or $10^{-4}$ mbar*l/s, preferably even a helium seal tightness of less than $10^{-5}$ mbar*l/s or $10^{-6}$ mbar*l/s. On the other hand, terms such as "seal", "sealed" etc. are not to be interpreted too narrowly such that a merely macroscopic closure may also be comprised. Even a possibly remaining leakage through the interior of a, in particular tubular, insulation of the connecting cable or connecting cables is disregarded for present purposes since this leakage may be sealed at another location, for example at a plug connected to the connecting cable and connecting cables. It is also possible to provide for conducting such a leakage through the connecting cable or through the connecting cables into a non-critical area, for example a colder and less exposed area of a motor vehicle. Although an absolute or hermetic seal tightness (in particular a helium seal tightness of less than 10^−10 mbar*I/s is in principle possible, it is prohibitive in terms of cost, as it were, with the exception of special applications.

The present invention also relates to a method for manufacturing a cable passage for sealing and for electrically contacting an exhaust-gas sensor, including a protective sleeve and including at least one connecting cable, which is run out of the protective sleeve on at least one front side of the protective sleeve, in particular for manufacturing a cable passage as recited in one of claims 1 through 14 or an exhaust-gas sensor as recited in claim 15, characterized by the introduction of a liquefied fluoropolymer-containing material into the space existing between the protective sleeve and the at least one connecting cable.

The liquefied fluoropolymer-containing material may be in particular a thermoplastically workable fluoropolymer-containing material.

The method according to the present invention for manufacturing a cable passage for sealing and for electrically contacting an exhaust-gas sensor, including a protective sleeve and including at least one connecting cable, which is run out of the protective sleeve on at least one front side of the protective sleeve, in particular for manufacturing a cable passage as recited in one of claims 1 through 14 or an exhaust-gas sensor as recited in claim 15, may, additionally or alternatively, have in particular one or multiple of the following method steps, for example in the indicated order.

Providing an in particular metallic protective sleeve, in particular in the form of a tube that is open on one or two sides Anchoring at least one connecting cable laterally in the interior of the protective sleeve, for example with the aid of a holder, as described above and/or in the exemplary embodiments, or with the aid of a separate guide piece, as described above and/or in the exemplary embodiments, or with the aid of a passage hole of the protective sleeve, as described above and/or in the exemplary embodiments.

Connecting, in particular connecting in a force-locking and/or integral and/or form-locking manner, the exhaust-gas-side end of the at least one connecting cable to at least one contact of an in particular ceramic sensor element of the exhaust-gas sensor, in particular to at least one elastic connecting element fastened on the exhaust-gas-side end of the at least one connecting cable.

Welding the protective sleeve to the housing body of the exhaust-gas sensor, in particular by laser welding.

Introducing a liquefied molten compound or injection-molding compound made of a thermoplastic fluoropolymer, in particular at a temperature between 240 and 320° C. or a temperature between 290 and 320° C., into the space existing between the protective sleeve and the at least one connecting cable through the front-side opening of the protective sleeve, out of which the at least one connecting cable is run, for example by injection or immersion, such that in the subsequent cooling of the thermoplastically workable fluoropolymer-containing material, an in particular integral seal is created between the protective sleeve and the at least one connecting cable, in particular through the thermoplastically workable fluoropolymer-containing material.

In a special variant of the manufacturing method, the order of the two latter method steps is reversed. That is to say that the introduction of the liquefied molten compound or the injection-molding compound made of thermoplastic fluoropolymer occurs prior to the protective sleeve being welded together with the housing body of the exhaust-gas sensor. In other words, first a cable passage according to the present invention is produced, and it is subsequently joined with the housing body of an exhaust-gas sensor to form an exhaust-gas sensor according to the present invention.

DETAILED DESCRIPTION OF THE INVENTION

Figure 1A:
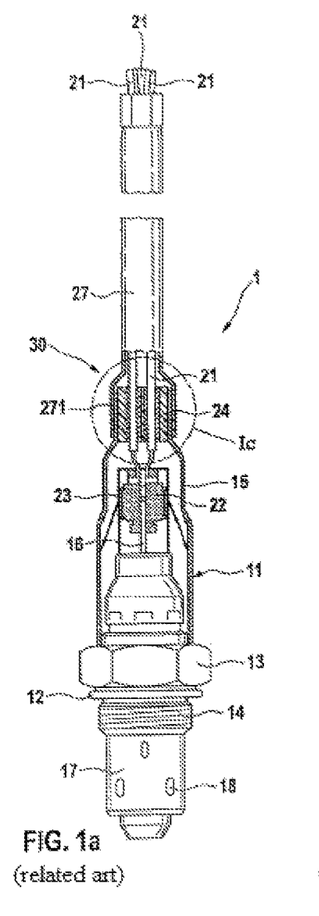
FIGS. 1a, 1b and 1c show an example of an exhaust-gas sensor known from the related art having an associated cable passage.
Figure 1B:
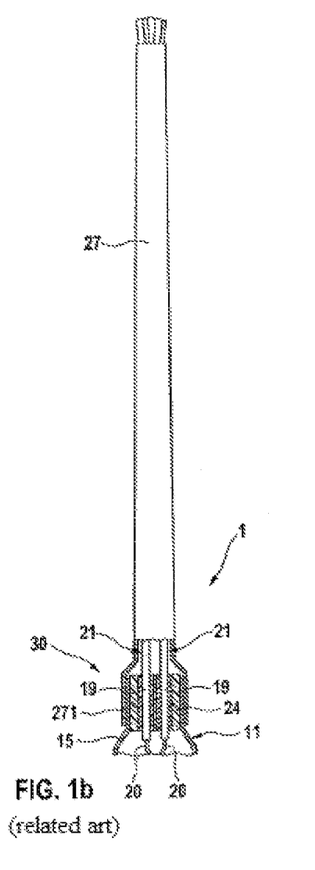
Figure 1C:
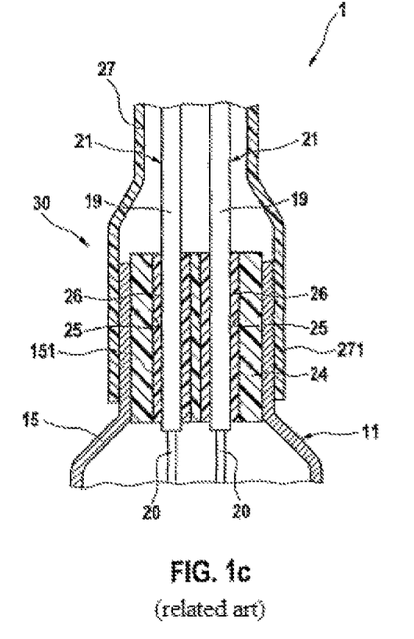

FIGS. 1a, 1b and 1c show an example of an exhaust-gas sensor known from the related art having an associated cable passage 30.

The exhaust-gas sensor 1 shown in a side view and in a partially sectional view in FIG. 1a by way of example is conceived as a lambda probe for measuring the oxygen concentration for example in the exhaust gas of burners or internal combustion engines. However, it may also be developed as a temperature sensor or as a pressure gage or as sensor for measuring the nitrogen-oxide concentration or soot particle concentration in the exhaust gas. Exhaust-gas sensor 1 has a housing 11. Housing 11 is made of a solid hollow housing body 12 made of metal having a screw thread 14 and an installation hex bolt 13 for screwing housing body 12 into a connecting piece situated on the exhaust-gas pipe of an internal combustion engine or a burner and a protective sleeve 15 slipped over housing body 12 and firmly connected to it. Situated in housing 11 is a sensor element 16, which projects from housing 11 by a measuring-gas-side end and is covered there by a protective tube 17, which has gas-passage holes 18 and is fastened on the exhaust-gas side on housing body 12. An the connection-side end, which faces away from the end on the measuring-gas side, sensor element 16 has contact surfaces, which are connected (not shown here) via circuit traces to measuring electrodes situated at the end on the measuring-gas side. Electrical conductors 20 of connecting cables 21, which are enclosed by insulation 19 in the form of an insulating jacket, are contacted on the contact surfaces. A two-part ceramic clamping body 22 is provided for contacting contact surfaces and electrical conductors 20, which is surrounded on the outside by a spring element 23 and which presses electrical conductors 20 onto the contact surfaces of sensor element 16 in a force-locking manner. Ceramic clamping body 22 is radially supported on protective sleeve 15.

In an end section 151 of protective sleeve 15, which is reduced in diameter, a prefabricated stopper 24, made for example of polytetrafluoroethylene (PTFE), is inserted, which has a number of axial passage channels 25 corresponding to the number of connecting cables 21. Connecting cables 21, which are anchored with their electrical conductors 20 on sensor element 16 in a force-locking manner, are run through passage channels 25 and emerge from protective sleeve 15 at the end of prefabricated stopper 24. In order to achieve sufficient seal tightness at the cable exit even at higher temperatures, insulation 19 developed as an insulating jacket of connecting cables 21 made of a fluorine-containing material is welded at least in places to the channel wall of passage channels 25. In FIG. 1a—as may be seen in the enlarged sectional view of FIG. 1c—the inside diameter of passage channels 25 is greater than the outer diameter of connecting cables 21. A welding tube 26 is respectively slipped over the cable sections in the passage channels 25, which together with the respective connecting cable 21 is pulled into the associated passage channel 25 of prefabricated stopper 24. When suitably heated, welding tube 26 fuses with the material of insulation 19 developed as an insulating jacket on the one hand and with the material of prefabricated stopper 24 on the other hand so as to produce both a high seal tightness of the cable exit point and also high resistance against the cable being pulled out of housing 11.

From the point of exit from the housing, connection cables 21 are accommodated in a shared shrink tube 27, which is slipped over end section 151 of protective sleeve 15 by its housing-side tube end section 271. By preheating shrink tube 27 or end section 151 of protective sleeve 15, shrink tube 27 shrinks and is pressed onto end section 151 in a sealing manner. Shrink tube 27 may have one or a plurality of layers and is made of a material that has mechanical, physical and chemical properties comparable to fluorine-containing plastics. In FIG. 1a, shrink tube 27 has an approximately constant inside diameter across its length enclosing connecting cables 21. In FIG. 1b, the inside diameter of shrink tube 27 tapers from the end on the housing side to the end on the plug side.

Altogether, cable passage 30 shown in FIGS. 1a, 1b and 1c and already known from the related art comprises a multitude of components, which have to be handled discretely when manufacturing cable passage 30 or when manufacturing the associated exhaust-gas sensor 1, must be brought into the desired relative position to one another, and finally must also be connected. Aside from protective sleeve 15 and connecting cables 21, these components are in particular the prefabricated stopper 21, welding tubes 26 and shrink tube 27. Manufacturing the cable passage 30 or manufacturing associated exhaust-gas sensor 1 is thus comparatively complex and expensive.

By contrast, the exemplary embodiments of exhaust-gas sensors 1 according to the present invention or cable passages 30 according to the present invention shown in FIGS. 2 through 7 differ from cable passage 30 known from the related art or exhaust-gas sensors 1 known from the related art by the fact that at least one cross section of the space existing between protective sleeve 15 and the at least one connecting cable 21 is filled with a thermoplastically workable fluoropolymer-containing material 31. Since in particular only one thermoplastically workable fluoropolymer-containing material 31 is provided, the latter may be introduced, in particular with little manufacturing effort, for example in a liquid or liquefied state, into the space existing between the protective sleeve and the at least one connecting cable, in particular by pouring the thermoplastically workable fluoropolymer-containing material 31, by injection molding or extrusion coating with the thermoplastically workable fluoropolymer-containing material 31 or by immersing the front side of protective sleeve 15 into the thermoplastically workable fluoropolymer-containing material 31.

The exemplary embodiments of exhaust-gas sensors 1 according to the present invention or cable passages 30 according to the present invention shown in FIGS. 2 through 7 differ additionally or alternatively from cable passage 30 known from the related art or from exhaust-gas sensors 1 known from the related art by lacking a prefabricated stopper, as the exhaust-gas sensor 1 from the related art (reference numeral 24) has, which is shown in FIGS. 1a, 1b and 1c. In exhaust-gas sensors 1 according to the present invention, the missing prefabricated stopper is replaced by a fluoropolymer-containing material 31, which is introduced into the interior of protective sleeve 15 in a liquid state, which represents in particular a cable outlet 30 manufactured in accordance with the independent method claim. The fluoropolymer-containing material 31 used for this purpose is in particular thermoplastically workable, in particular in the temperature range from 240° C. to 320° C.

Figure 2A:
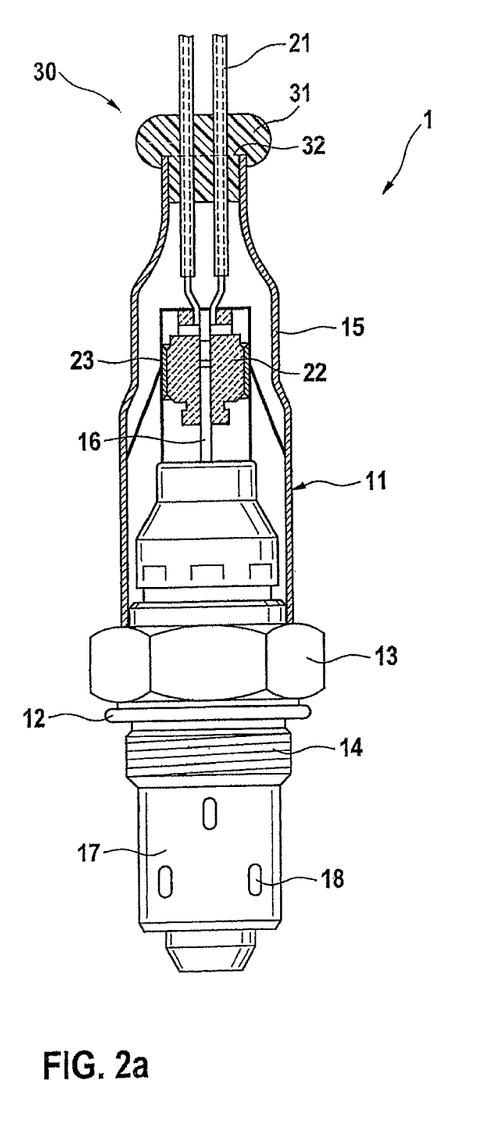
FIGS. 2a, 2b and 2c show a first exemplary embodiment of the present invention.

FIG. 2a shows a first exemplary embodiment of an exhaust-gas sensor 1 according to the present invention, which differs from exhaust-gas sensor 1 from the related art shown in FIGS. 1a, 1b and 1c by its cable passage 30 according to the present invention. Cable passage 30 according to the present invention is also shown in accordance with the first exemplary embodiment in FIG. 2b in an enlarged and more detailed manner. Regarding the construction of exhaust-gas sensor 1 of the present invention, reference may be made to FIG. 1a and the associated description, with the exception of what concerns the cable passage 30.

Cable passage 30 according to the first exemplary embodiment has a protective sleeve 15, which is a tube having an axial symmetry, which is connected on its side facing the exhaust gas to a housing body 12, for example welded by laser beam. In this example, protective sleeve 15 is a deep-drawn part made of stainless steel having a wall thickness of 0.4 mm to 0.5 mm. Protective sleeve 15 tapers toward the side facing away from the exhaust gas; continuous and/or single-stepped or multi-stepped profiles of the protective tube being possible in particular. On the side facing away from the exhaust gas (top of FIGS. 2a and 2b), protective tube 11 has an open, initially still unsealed front side 32.

Figure 2B:
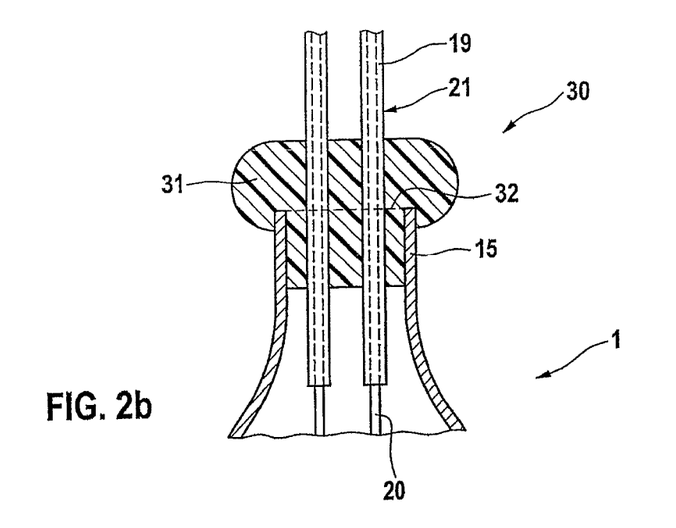

Cable passage 30 according to the present invention has for example four connecting cables 21 that are spaced apart from one another, of which respectively two may be seen in FIGS. 2a and 2b. Alternatively, of course, another number of connecting cables 21 or even only one connecting cable 21 may be provided instead of four connecting cables 21. Connecting cables 21 respectively have one electrical conductor 20, which in the present case is made of stranded copper wire or stranded steel-copper wire, and furthermore an insulation 19, which radially surrounds electrical conductor 20 in the area of cable passage 30, in particular in a jacket-shaped manner. Insulations 19 are in the present case developed as insulating jackets and are made of polytetrafluoroethylene (PTFE), which has a comparatively high temperature resistance. Including insulation 19, the diameter of connecting cables 21 is 1 mm for example such that in the present case connecting cables 21 are cables suitable, for example, for conducting currents of several, for example 2 or 5, amperes maximally. The distances of neighboring connecting cables 21 from one another and from protective sleeve 15 in this example are 1 mm in the area of the cable passage. The present invention provides for connecting cables 21 to be run out of protective sleeve 15 on the front side 32 of protective sleeve 15.

A cross section of the space existing between protective sleeve 15 and connecting cables 21 is filled with a thermoplastically workable fluoropolymer-containing material 31. In this exemplary embodiment, an area of protective sleeve 15 is filled completely, which extends from the front side 32 of protective sleeve 15 several, for example 5 to 10, millimeters into the direction of protective sleeve 15 facing the exhaust gas. Furthermore, thermoplastically workable fluoropolymer-containing material 31 protrudes axially in the direction facing away from the exhaust gas and laterally beyond the front side 32 of protective sleeve 15, likewise by respectively several, for example respectively 1 to 3, millimeters.

In this exemplary embodiment, thermoplastically workable fluoropolymer-containing material 31 is an, in particular homogeneous, perfluoroalkoxy polymer polyblend, whose melting range lies between 260° C. and 320° C., in particular between 260° C. and 320° C. The use of perfluoroalkoxy polymer polyblends having molar masses of, in particular exclusively, $3*10^5$ to $3*10^6$ g/mol is preferred. Other perfluoroalkoxy polymer polyblends or perfluoroalkoxy polymers (PFA) may in principle also be considered, likewise the thermoplastically workable fluoropolymer-containing materials tetrafluoroethylene-perfluoropropylene (FEP), polychlorotrifluoroethylene (PCTFE) and polyvinylidene fluoride (PVDF).

Polytetrafluoroethylene (PTFE), fluororubbers (FKM), perfluororubbers (FFKM), tetrafluoro ethylene/propylene rubbers (FEPM) and fluorinated silicone rubbers, by contrast, are not thermoplastically workable fluoropolymer-containing materials and do not fall within the scope of the present invention, and are in particular not used in the present context to fill a cross section of the space existing between protective sleeve 15 and connecting cables 21.

For manufacturing the cable passage 30 in accordance with this first exemplary embodiment (FIG. 2c), connecting cables 21 are run through the front side 32 of a protective sleeve 15 and are anchored axially and laterally in the protective sleeve with the aid of an auxiliary part 40, which either remains or is later removed or is removable. Auxiliary part 40 also effects an at least provisional seal and/or division of protective sleeve 15 between its two axial ends. Subsequently, an injection molding die 41 is used to introduce the liquefied, in particular thermoplastically workable fluoropolymer-containing material 31, which is present as molding compound 311, into the space existing between protective sleeve 15 and connecting cables 21, which is separated by auxiliary part 40 within protective sleeve 15 facing away from the exhaust gas. Once cooled, the introduced molding compound 311 forms the solidified thermoplastically workable fluoropolymer-containing material 31.

Alternative manufacturing processes are likewise possible. Thus, the device prepared as in FIG. 2c may also be immersed, once or repeatedly, vertically or at an angle of 45° against the horizontal, front side 32 first, into a molten compound of thermoplastically workable fluoropolymer-containing material 31. As a consequence of cooling, the molten mass solidifies in the area of protective sleeve 15 and thus solidified thermoplastically workable fluoropolymer-containing material 31 forms in the space existing between protective sleeve 15 and connecting cables 21, which is separated by auxiliary part 40 within protective sleeve 15 facing away from the exhaust gas. In particular, an integral connection is formed between thermoplastically workable fluoropolymer-containing material 31 and connecting cable 21. In particular, an integral connection is formed between thermoplastically workable fluoropolymer-containing material 31 and protective sleeve 11. In particular, an overall integral seal of cable passage 31 is formed.

Figure 2C:
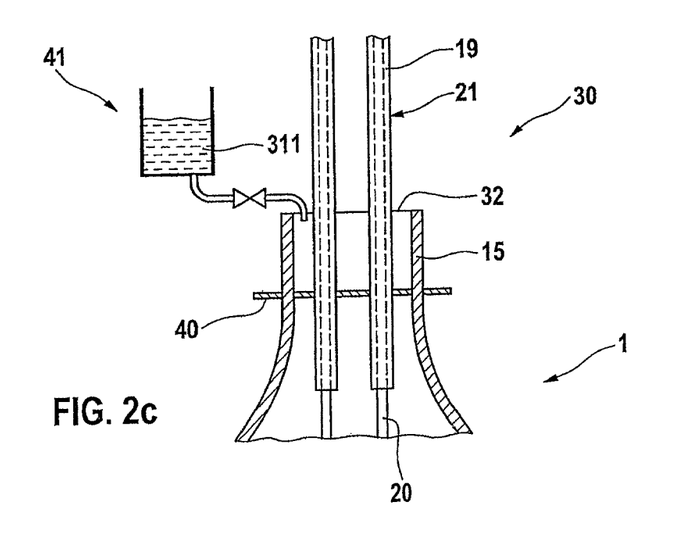

For manufacturing exhaust-gas sensor 1 as shown in FIG. 2a, the above-described cable passage 31 is welded to the housing body 12, for example using a laser beam. Alternatively, it would also be possible to weld the not-yet-finished cable passage 30, for example as it is shown in FIG. 2c, to housing body 12, for example using a laser beam, and to introduce thermoplastically workable fluoropolymer-containing material 31 only subsequently, for example as described previously for cable passage 30.

Alternative specific embodiments of the first exemplary embodiment provide for protective sleeve 15 to taper particularly strongly on its side facing away from the exhaust gas, in the area of its front side (top of FIGS. 2a and 2b), and for the gaps between the connecting cables 21 (in the case of multiple connecting cables 21) and between the connecting cable(s) and the protective sleeve 15 to be narrower. For example, the distance between neighboring connecting cables 21 and between connecting cable(s) 21 and protective sleeve 15 may be 0.35 mm in this example.

According to a second exemplary embodiment, cable passages 30 or exhaust-gas sensors 1 are provided, which are developed further on the basis of cable passages 30 or exhaust-gas sensors 1 of the first exemplary embodiment by providing a, for example metallic, holder 33 in the interior of protective tube 11. Holder 33 is in particular clamped with protective sleeve 15 and/or welded, for example welded using a laser beam.

Figure 3A:
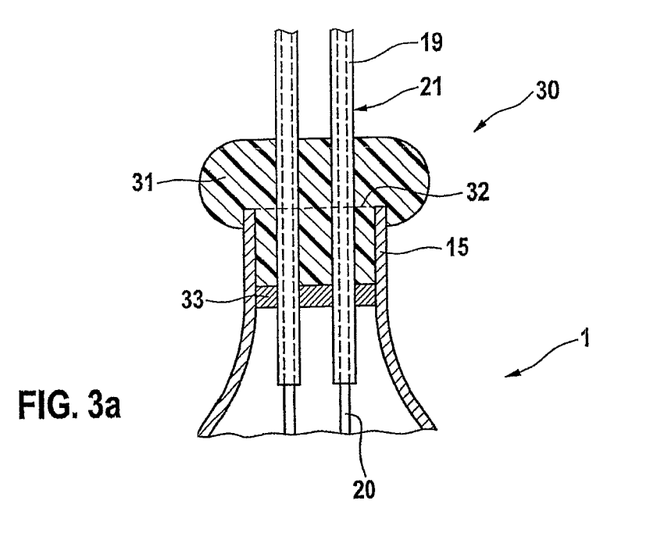
FIGS. 3a, 3b, 4a and 4b show a second exemplary embodiment of the present invention.
Figure 3B:
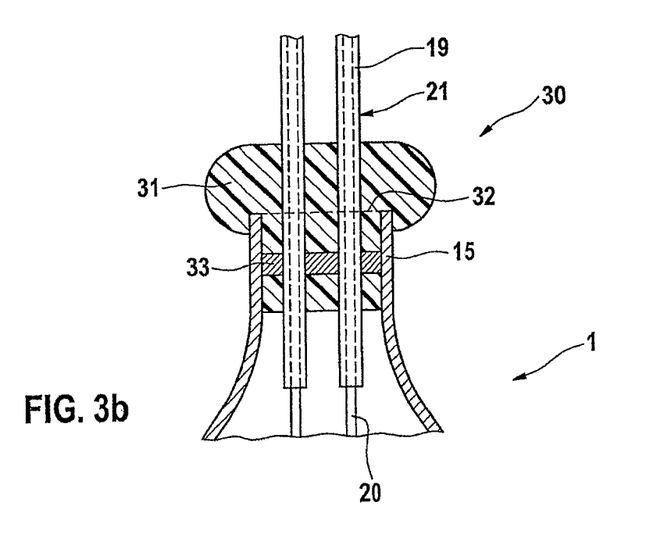

The holder 33 shown in FIG. 3b is situated in the axial direction within the thermoplastically workable fluoropolymer-containing material, for example centrally, and anchors connecting cables 21 laterally and axially. By contrast, the holder 33 shown in FIG. 3a is situated on the exhaust-gas side (bottom of FIG. 3a) of the thermoplastically workable fluoropolymer-containing material 31. It thus effects also an axial support and/or fastening of the thermoplastically workable fluoropolymer-containing material 31, and does so on the one hand in the finished product, in which the thermoplastically workable fluoropolymer-containing material 31 is in a solid state, and, on the other hand, during the manufacture of the cable passage or during the manufacture of exhaust-gas sensor 1. In the latter, holder 33 prevents the thermoplastically workable fluoropolymer-containing material 31 from penetrating too deeply into the interior of the cable passage or exhaust-gas sensor 1, in a similar manner as the auxiliary part 40 (FIG. 2c) discussed in connection with the first exemplary embodiment.

Figure 4A:
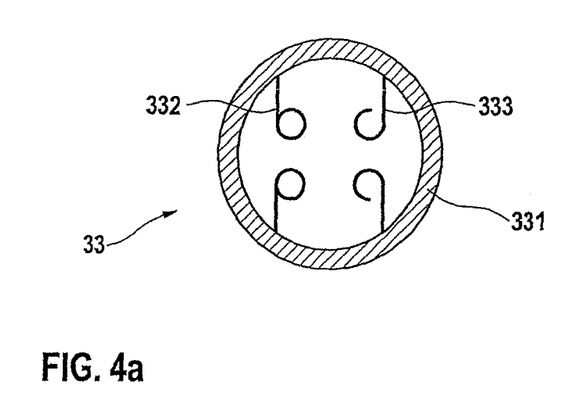
Figure 4B:
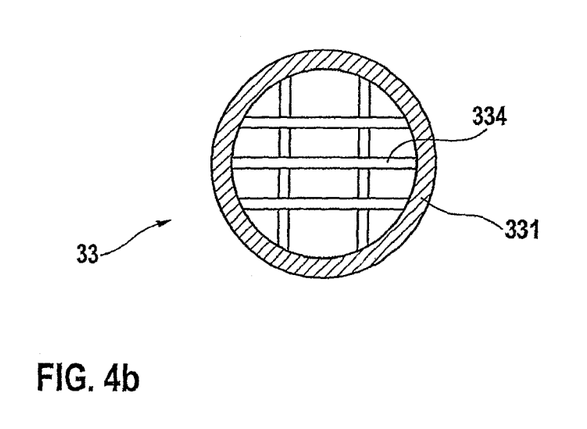

Examples of holders 33 are shown in a top view in FIGS. 4a and 4b. Holders 33 are developed as inserts and have means for fastening them in protective sleeve 15, in the present example a metallic outer annular section 331 that may be welded or clamped to protective sleeve 15. Holders 33 in these examples furthermore have respectively means for anchoring connecting cables 21 and for supporting and/or fastening thermoplastically workable fluoropolymer-containing material 31. These are developed in the specific embodiment shown in FIG. 4a as eyelets 332 or hooks 333, while in the specific embodiment shown in FIG. 4b they are formed by intersecting webs 334.

For manufacturing cable passages 30 or exhaust-gas sensors 1 according to the second exemplary embodiment, reference may be made on the one hand to what was said in connection with the manufacture of cable passages 30 or exhaust-gas sensors 1 according to the first exemplary embodiment, additional method steps being presently necessary in connection to the arrangement and anchoring of holder 33 in protective tube 11 and in the anchoring of connecting cables 21 in the means of holder 33 provided for this purpose. To this end, connecting cables 33 are for example inserted, hooked, threaded and/or the like through eyelets 331, hooks 332, webs 333 and/or so on.

Figure 5A:
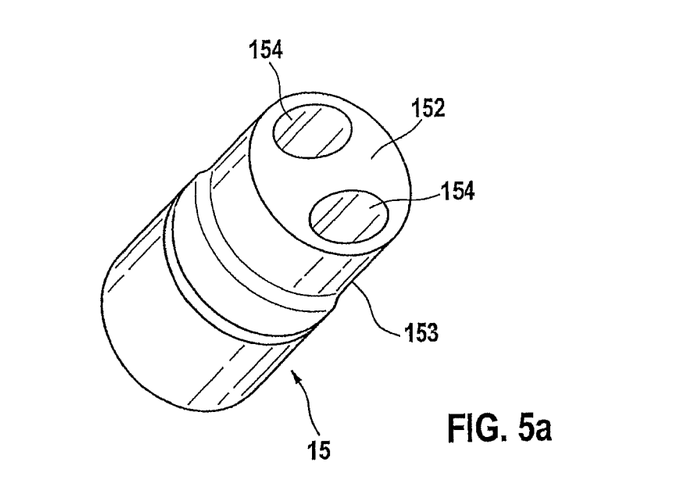
FIGS. 5a and 5b show a third exemplary embodiment of the present invention.

In the cable passages 30 or exhaust-gas sensors 1 shown presently in the exemplary embodiments and specific embodiments of this application, it is always possible to use a cup-shaped protective sleeve 15, as shown in FIG. 5a for example.

Cup-shaped protective sleeve 15 has a bottom 152 and a wall 153 encircling its edge or situated and fastened circumferentially around its edge. In the example, two elongated parallel passage openings 154 are provided in bottom 152 of cup-shaped protective sleeve 15, through which the for example two connecting cables 21 are able to run. When using a cup-shaped protective sleeve 15 and at least one connecting cable 21 that is run through a passage opening 154 in the bottom 152 of this protective sleeve, it is preferred that the thermoplastically workable fluoropolymer-containing material 31 is situated in the area of passage opening 154 and in that location fills at least one cross section of the space existing between protective sleeve 15 and the at least one connecting cable 21, as in cable passage 30 shown in perspective in FIG. 5b, which represents the third exemplary embodiment of the present invention.

Figure 5B:
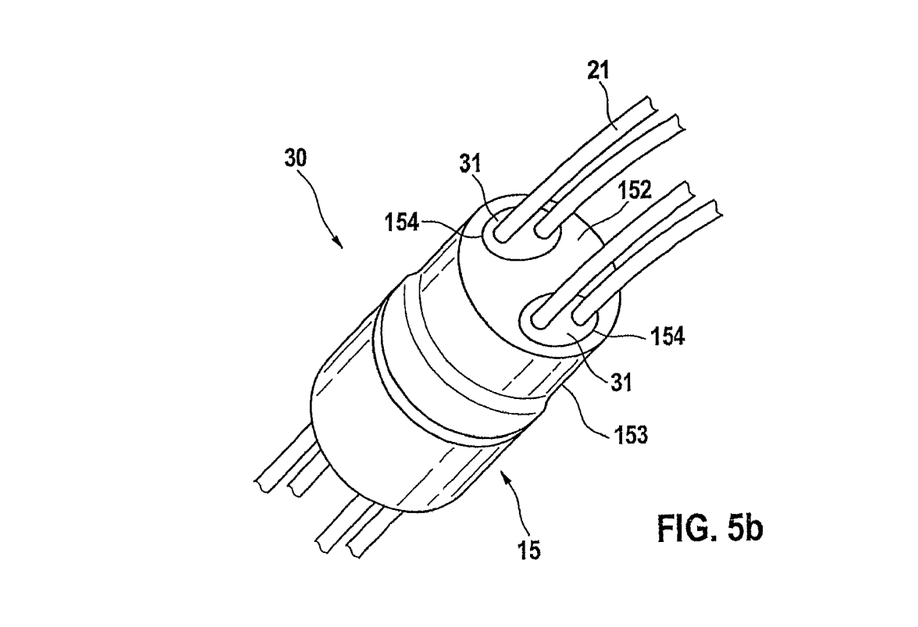

The advantage of using such a cup-shaped protective sleeve 15 or such a cable passage 30 according to the third exemplary embodiment lies in the fact that the open cross section of passage openings 154 is markedly reduced in comparison to the cross section of protective tube 15 away from the cup bottom 152 or in comparison to the surface area of the bottom 152 of the cup, to 25% in this example. It is thus possible to seal protective sleeve 15 using a comparatively small amount of thermoplastically workable fluoropolymer-containing material 31 and to do so in a mechanically particularly stable manner.

According to a fourth exemplary embodiment, cable passages 30 or exhaust-gas sensors 1 are provided, which are developed further on the basis of cable passages 30 or exhaust-gas sensors 1 of the previous exemplary embodiment by providing a separate guide piece 34.

Separate guide piece 34 is used to guide and anchor connecting cables 21 among one another axially and laterally, on the one hand on the finished exhaust-gas sensor 1 or on the finished cable passage 30, in particular, however, already at a time of preassembly, at which the connecting cables 21 jointly and jointly with guide piece 34 are fed into protective sleeve 15.

Figure 6A:
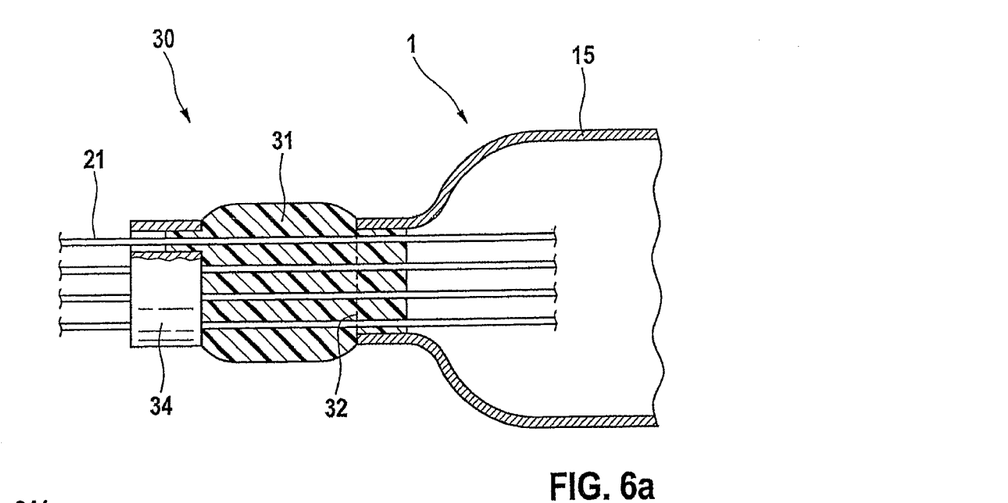
FIGS. 6a, 6b, 6c, 7a and 7b show a fourth exemplary embodiment of the present invention.
Figure 6B:
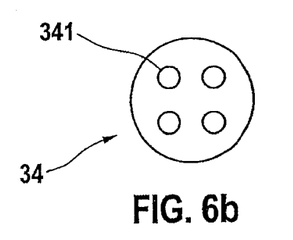

A first specific embodiment of the fourth exemplary embodiment of an exhaust-gas sensor 1 of the present invention or of a cable passage 30 of the present invention is shown in FIG. 6a. FIG. 6b shows a top view of associated guide piece 34.

Guide piece 34 is in this example a disk of a thickness of several, for example 1.5 to 4.5 millimeters, the diameter of which agrees for example with the end face 32 of protective sleeve 15. Guide piece 34 is made for example from metal, for example from stainless steel. Guide piece 34 has a number of holes 341 corresponding to the number of connecting cables 21 to be guided. Optionally, thermoplastically workable fluoropolymer-containing material 31 may be situated at least partially in the area of holes 341 of guide piece 34.

Guide piece 34 is situated in particular at a distance from protective sleeve 15, in particular in this example, thermoplastically workable fluoropolymer-containing material 31 is situated partially axially between guide piece 34 and protective sleeve 15, namely, in this example, is respectively integrally connected to guide piece 34 and protective sleeve 15.

Alternatively or additionally, guide piece 34 may also be laterally distanced from protective sleeve 15. In the specific embodiment shown in FIG. 6c, guide piece 34 is inserted into the interior of protective sleeve 15. In the process, a circular gap between guide piece 34 and protective sleeve 15 is filled in an integral manner with thermoplastically workable fluoropolymer-containing material 31.

Figure 6C:
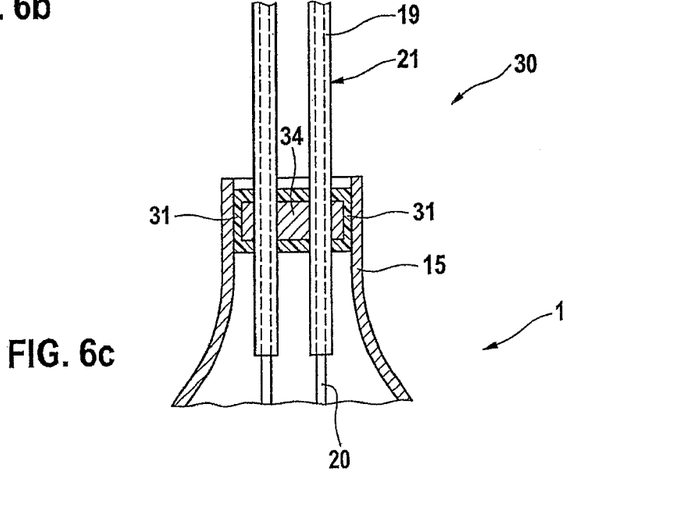

The manufacture of the cable passages 30 or associated exhaust-gas sensors 1 shown in FIGS. 6a and 6c occurs in accordance with what was said with respect to the previous exemplary embodiments.

Figure 7A:
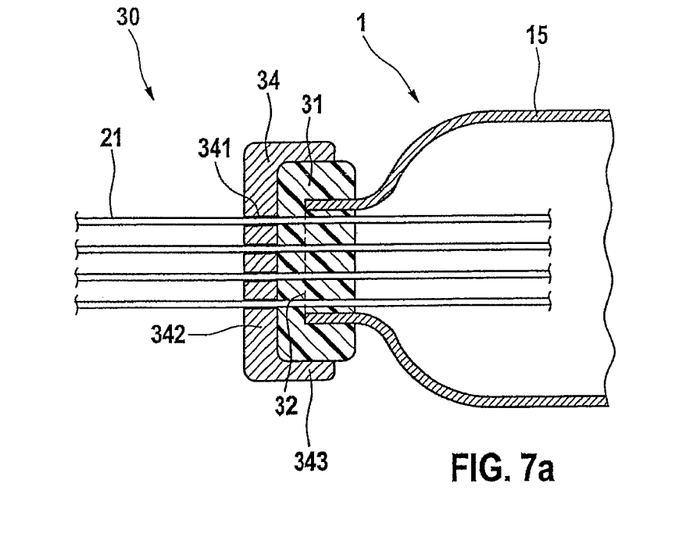

In another specific embodiment of the fourth exemplary embodiment of a cable passage 30 according to the present invention or of an exhaust-gas sensor 1 according to the present invention, a cup-shaped guide piece 34 is used, which is made up of a guide piece bottom 342 having holes 341 and an encircling guide piece wall 343 that is firmly attached to guide piece bottom 342 and pointing from the latter to the exhaust-gas side. Cup-shaped guide piece 34 is slipped, guide piece wall 343 first, onto the front side 32 of protective sleeve 15. In the process, a circular gap between guide piece 343 and protective sleeve 15 is filled in an integral manner with thermoplastically workable fluoropolymer-containing material 31 (FIG. 7a).

Figure 7B:
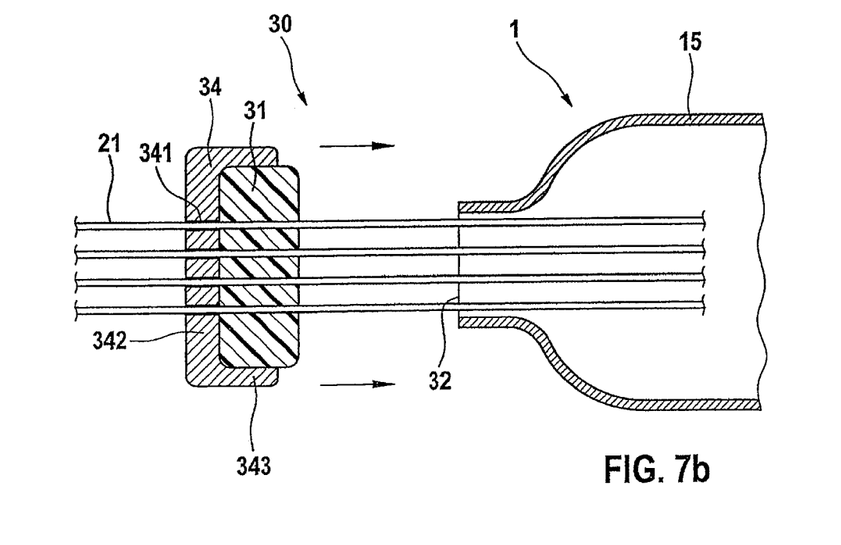

The manufacture of a cable passage 30 according to the additional specific embodiment of the fourth exemplary embodiment is possible in a particularly elegant manner (see FIG. 7b). For this purpose, thermoplastically workable fluoropolymer-containing material 30 is filled initially in liquid form into cup-shaped guide piece 34 or corresponding solid material is liquefied in that location. For this purpose, guide piece wall 343 points from guide piece bottom 342 upward, against the force of gravity (to the right in FIG. 7b). Subsequently, cup-shaped guide piece 34 is slipped onto protective sleeve 15 by relative movement such that the cable passage shown in FIG. 7a is formed following the solidification of thermoplastically workable fluoropolymer-containing material 31.

In variants of the manufacturing process it is also possible to insert thermoplastically workable fluoropolymer-containing material 30, for example in the form of a capsule, initially in solid form into cup-shaped guide piece 34 and to liquefy it only during or after the process of slipping cup-shaped guide piece 34 onto protective sleeve 15.

Moreover, it is always possible, alternatively or additionally, to bring thermoplastically workable fluoropolymer-containing material 30 in a solid state, in particular in the form of a capsule, to the location of the seal to be created in the interior of protective tube 15, to melt it in that location such that it is brought into the desired shape, and subsequently to solidify it in this shape.

What is claimed is:
1. A cable passage for sealing and for electrically contacting an exhaust-gas sensor, comprising:

a protective sleeve; and
  at least one connecting cable which is run out of the protective sleeve on at least one front side of the protective sleeve, wherein at least one cross section of a space existing between the protective sleeve and the at least one connecting cable is filled with a thermoplastically workable fluoropolymer-containing material,
  wherein the at least one cross section is inside the protective sleeve.

2. The cable passage as recited in claim 1, wherein the thermoplastically workable fluoropolymer-containing material has at least one of perfluoroalkoxy polymer, a tetrafluoroethylene-perfluoropropylene, a polychlorotrifluoroethylene, a polyvinylidene fluoride, a perfluoroalkoxy polymer, a tetrafluoroethylene-perfluoropropylene, a polychlorotrifluoroethylene, and a polyvinylidene fluoride.

3. The cable passage as recited in claim 2, wherein the thermoplastically workable fluoropolymer-containing material has a melting point between 260° C. and 320° C.

4. The cable passage as recited in claim 2, wherein the thermoplastically workable fluoropolymer-containing material is integrally connected to at least one of the connecting cable and the protective sleeve.

5. The cable passage as recited in claim 4, wherein the thermoplastically workable fluoropolymer-containing material is homogeneous.

6. The cable passage as recited in claim 4, wherein the thermoplastically workable fluoropolymer-containing material is introduced in a liquid state into the space existing between the protective sleeve and the at least one connecting cable.

7. The cable passage as recited in claim 4, wherein the thermoplastically workable fluoropolymer-containing material is introduced in a solid state into the space existing between the protective sleeve and the at least one connecting cable and is subsequently molten.

8. The cable passage as recited in claim 2, further comprising:
  a metallic holder for at least one of (i) holding the at least one connecting cable at least one of laterally and axially, and (ii) supporting the thermoplastically workable fluoropolymer-containing material in the axial direction.

9. The cable passage as recited in claim 8, wherein the holder is integrally connected to the protective sleeve.

10. The cable passage as recited in claim 2, wherein the protective sleeve is cup-shaped and at least one passage opening is provided in the bottom of the cup-shaped protective sleeve, through which the at least one connecting cable is run, and the thermoplastically workable fluoropolymer-containing material is provided at least partially in the area of the passage opening in the bottom of the cup-shaped protective sleeve.

11. The cable passage as recited in claim 2, wherein the cable passage has a guide piece separate from the protective sleeve for the at least lateral guidance of the at least one connecting cable, the thermoplastically workable fluoropolymer-containing material being situated at least one of partially axially and partially laterally between the guide piece and the protective sleeve.

12. The cable passage as recited in claim 11, wherein the guide piece is disk-shaped and has at least one hole through which the at least one connecting cable is run, the thermoplastically workable fluoropolymer-containing material being at least partially situated in the area of the hole of the guide piece.

13. The cable passage as recited in claim 11, wherein the guide piece is cup-shaped and has a bottom with at least one hole through which the at least one connecting cable is run, the thermoplastically workable fluoropolymer-containing material being at least partially situated in the interior of the cup-shaped guide piece, and the cup-shaped guide piece being slipped with its open side over the front side of the protective sleeve.

14. The cable passage as recited in claim 11, wherein the guide piece is integrally connected by the thermoplastically workable fluoropolymer-containing material to the protective sleeve.

15. An exhaust-gas sensor, comprising:
  a housing body; and
  a cable passage connected on a side of the housing facing away from the exhaust gas, wherein the cable passage includes a protective sleeve and at least one connecting cable which is run out of the protective sleeve on at least one front side of the protective sleeve, wherein at least one cross section of a space existing between the protective sleeve and the at least one connecting cable is filled with a thermoplastically workable fluoropolymer-containing material,
  wherein the at least one cross section is inside the protective sleeve.

16. The cable passage as recited in claim 1, wherein the at least one cross section comprises a plane parallel to the longitudinal axis of the protective sleeve and includes the at least one front side of the protective sleeve.

17. The exhaust-gas sensor as recited in claim 15, wherein the at least one cross section comprises a plane parallel to the longitudinal axis of the protective sleeve and includes the at least one front side of the protective sleeve.

* * * * *